United States Patent
Alaofi et al.

(10) Patent No.: US 12,419,856 B1
(45) Date of Patent: *Sep. 23, 2025

(54) METHOD OF TREATING MIDDLE EAST RESPIRATORY SYNDROME (MERS)

(71) Applicant: KING SAUD UNIVERSITY, Riyadh (SA)

(72) Inventors: Ahmed Lafi Alaofi, Riyadh (SA); Mudassar Ahmad Shahid, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/985,161

(22) Filed: Dec. 18, 2024

Related U.S. Application Data (63) Continuation of application No. 18/654,709, filed on May 3, 2024, now Pat. No. 12,208,082.

(51) Int. Cl.
*A61K 31/353* (2006.01)
*A61P 31/14* (2006.01)
*C12N 9/99* (2006.01)

(52) U.S. Cl.
CPC ............ *A61K 31/353* (2013.01); *A61P 31/14* (2018.01); *C12N 9/99* (2013.01)

(58) Field of Classification Search
CPC .......... A61K 31/353; A61P 31/14; C12N 9/99
See application file for complete search history.

(56) References Cited

U.S. PATENT DOCUMENTS 12,208,082 B1 * 1/2025 Alaofi ................. A61P 31/14
2021/0283162 A1 * 9/2021 Coe .................... A61K 31/045

OTHER PUBLICATIONS

Baéz-Santos et al. Catalytic Function and Substrate Specificity of the Papain-Like Protease Domain of nsp3 from the Middle East Respiratory Syndrome Coronavirus J Virol. Nov. 2014;88(21):12511-12527 (Year: 2014).*

Lasker, et al., "Search for Therapeutics Against COVID 19 Targeting SARS-COV-2 Papain-Like Protease: An in Silico Study", Preprint from Research Square, PPR172027 (2020).

Chaves, et al., "Agathisflavone, A Natural Biflavonoid That Inhibits SARS-COV-2 Replication by Targeting Its Proteases", Int. J. Biol. Macromol. 222: pp. 1015-1026 (2022).

Jo, et al., "Characteristics of Flavonoids as Potent MERS-COV 3C-LIKE Protease Inhibitors", Chemical Biology & Drug Design, 94(6): pp. 2023-2030 (2019).

* cited by examiner

*Primary Examiner* — Adam C Milligan
*Assistant Examiner* — William Y Lee
(74) *Attorney, Agent, or Firm* — Nath, Goldberg & Meyer; Joshua B. Goldberg

(57) ABSTRACT

A method of treating Middle East Respiratory syndrome (MERS) includes administering to a patient in need thereof a therapeutically effective amount of a pharmaceutical composition comprising fisetin and a pharmaceutically acceptable carrier.

4 Claims, 5 Drawing Sheets

Specification includes a Sequence Listing.

Buffer Tm 105.28°C

FIG. 2A

MERS-Plpro Tm 45.80°C

FIG. 2B

Metformin (774.23 µM) +MERS-Plpro Tm 43.66°C

FIG. 2C

FIS (43.67 µM)+MERS-Plpro Tm 32.73°C

METHOD OF TREATING MIDDLE EAST RESPIRATORY SYNDROME (MERS)

CROSS-REFERENCE TO RELATED APPLICATION

This application is a continuation of U.S. patent application Ser. No. 18/654,709, filed on May 3, 2024, the entire contents of which are incorporated herein by reference.

SEQUENCE LISTING

The instant application contains a Sequence Listing which has been submitted in XML format via Patent Center and is hereby incorporated by reference in its entirety. Said XML copy, created on Nov. 1, 2023, is named Sequence.xml and is 2000 bytes in size.

BACKGROUND

1. Field

The disclosure of the present patent application relates to method of treating Middle East Respiratory Syndrome (MERS) and, particularly, a method of treating Middle East Respiratory Syndrome (MERS) by binding of papain-like protease (PLpro)

2. Description of the Related Art

Middle East respiratory syndrome (MERS) is caused by a single-stranded, positive-sense RNA betacoronavirus (CoV). MERS or MERS-COV is a seriously fatal respiratory condition primarily prevalent in countries in the Middle East. For example, more than 70% of MERS cases have been diagnosed in Saudi Arabia. No therapeutic treatment has been previously identified for MERS. As such, efforts to stop the spread of MERS in healthcare facilities have been limited to infection prevention and control measures. Thus, MERS-COV is still an ongoing hazard to public health. Further, it is likely that the virus will evolve to improve its potential for pandemic spread and interhuman transmissibility.

In contrast to severe acute respiratory syndrome coronaviruses (SARS-COVs), which use angiotensin converting enzyme II (ACE-2) receptor, research on the genetic structure of MERS-COV revealed that the host-cell receptor for cell entrance was dipeptidyl-peptidase 4 (DPP4), commonly known as CD26. Historically, MERS-COV has no known pharmacological treatments and supportive care is the backbone of treatment. Numerous treatment strategies have been attempted that target different viral components either already in existence or being developed. The various types of available treatments symptomatic care, antiviral compounds, and immunotherapy using particular anti-MERS-COV antibodies. In cell culture, a number of medications, including ciclosporin and mycophenolic acid, suppress MERS-COV. Some substances such as chloroquine, chlorpromazine, loperamide, and lopinavir prevent the replication of viruses in test tubes, although it is unknown if patients will benefit from these medications.

Polyphenols from *Broussonetia papyrifera* and flavonoids like Herbacetin, isobavachalcone, quercetin 3-β-d-glucoside and helichrysetin were reported to inhibit the enzymatic activity of MERS-COV protease. Neuraminidase, Peptidomimetic inhibitors of enterovirus and GC376, a dipeptidyl transition, have been shown to inhibit MERS-PLpro, Silvestrol, GS-5734 (Remdesivir), resveratrol, nocodazole, loperamide, mycophenolic acid, and tyrosine kinase inhibitors saracatinib are other notable compounds which are reported to inhibit the replication of MERS-COV by different modes of action. Additionally, Doxorubicin (DOX), an anticancer agent, inhibited MERS-PLpro enzyme activity at IC50 value of 1.67 μM assumed DOX can be an effective antiviral agent against MERS-COV.

Protease blockers in in vitro testing on MERS-COV showed that lopinavir enhanced by ritonavir was effective. As a result, the FDA expanded the use of lopinavir for MERS-COV-infected patients. Since the structure of the MERS-PLpro blocking loop 2 (BL2) differs from that of the SARS-PLpro, when some SARS-PLpro inhibitors were tested against MERS-PLpro, none of them were effective. Consequently, it is important to create and test more lead molecules that are tailored for various viruses.

Thus, new drug candidates solving the aforementioned problems are desired.

SUMMARY

The present subject matter relates to a method of treating Middle East respiratory syndrome (MERS), including administering to a patient in need thereof a therapeutically effective amount of a pharmaceutical composition comprising a MERS-COV inhibitor. In an embodiment, the MERS-COV inhibitor can inhibit the activity of MERS-PLpro. In an embodiment, the MERS-COV inhibitor can include fisetin, having the following structural formula:

In a further embodiment, the present subject matter relates to use of a MERS-CoV inhibitor to inhibit the activity of MERS-PLpro. In an embodiment, the MERS-CoV inhibitor can bind to MERS-PL pro, and thereby, inhibit the activity of MERS-PL pro.

These and other features of the present subject matter will become readily apparent upon further review of the following specification.

BRIEF DESCRIPTION OF DRAWINGS

FIGS. 1A-1B are graphs depicting MERS protease inhibition by FIS (FIG. 1A) Percent inhibition.

FIGS. 3A-3C are graphs showing (FIG. 3A) root mean square deviation (RMSD); (FIG. 3B) root mean square fluctuation (RMSF)

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Throughout the application, descriptions of various embodiments use "comprising" language. However, it will be understood by one of skill in the art, that in some specific instances, an embodiment can alternatively be described using the language "consisting essentially of" or "consisting of".

As described herein, "room temperature" means a temperature of about 25° C.

The present subject matter relates to a method of treating Middle East respiratory syndrome (MERS), including administering to a patient in need thereof a therapeutically effective amount of a pharmaceutical composition comprising a MERS-COV inhibitor. In an embodiment, the MERS-COV inhibitor can inhibit the activity of MERS-papain-like protease (PLpro) (SEQ ID NO: 1).

In an embodiment, the MERS-COV inhibitor can include fisetin, having the following structural formula:

The structural features of fisetin (FIS: PubChem ID 5281614), which were first identified as an isolate from venetian sumach (*Rhus cotinus* L.), include two aromatic rings connected by a three-carbon oxygenated heterocyclic ring, four hydroxyl group substitutions, and one oxo group, which are primarily responsible for their biological activities. Fisetin is typically found in a variety of fruits and vegetables, including strawberries, apples, onions, and cucumbers, as well as in a number of Fabaceae and Anacardiaceae family trees and shrubs, as well as species of Quebracho colorado and Pinophyta. FIS is a potent senotherapeutic, chemopreventive, anti-inflammatory, antibacterial, anti-oxidant, and chemotherapeutic agent. There is little danger of harm from polyphenols because they are naturally present in food and have a long history of human use.

In an embodiment, the present subject matter relates to use of a MERS-COV inhibitor to inhibit the activity of MERS-PLpro. In an embodiment, the MERS-COV inhibitor can bind to MERS-PLpro and, thereby, inhibit the activity of MERS-PL pro.

One of the essential enzymes for a variety of viruses' transcription, maturation, and replication is protease. The identification of a protease inhibitory target, which is required for viral transcription and replication, has been the subject of numerous investigations. By specifically binding to viral proteases and preventing the proteolytic cleavage of the protein precursors required for the formation of infectious viral particles, protease inhibitors prevent viral replication. In CoVs, the papain-like protease (PLpro) and the 3-chymotrypsin-like protease (3CLpro), also known as the main proteases that are suitable targets for viral inhibitors, have been discovered. Both proteases are thought to play crucial roles in the replication of the virus and are therefore considered to be desirable targets for antiviral therapeutics.

An embodiment of the present subject matter is directed to use of a pharmaceutical composition including a MERS-COV inhibitor and a pharmaceutically acceptable carrier. To prepare the pharmaceutical composition, the MERS-COV inhibitors, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. One or more of the MERS-COV inhibitors can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of a MERS-CoV inhibitor or an amount effective to treat a disease, such as a coronavirus infection, may be determined initially from the Examples described herein and adjusted for specific targeted diseases using routine methods.

The MERS-COV inhibitor can be administered to a subject in need thereof. In an embodiment, the MERS-COV inhibitors can be administered to a subject in need thereof to inhibit MERS-COV infection, prevent MERS-COV transmission, and/or treat a MERS-COV infection. In these application the fisetin in the MERS-COV inhibitor binds to MERs-papain-like protease (PLpro) and inhibits the activity of PLpro, thereby providing the inhibition of MERS, prevention of MERS transmission, and/or treatment of a MERS infection.

An embodiment of the present subject matter is directed to a method of inhibiting MERS-COV infection, preventing MERS-COV transmission, and/or treating a MERS-CoV infection, comprising administering to a subject in need thereof a therapeutically effective amount of the pharmaceutical composition according to the present subject matter.

The MERS-COV inhibitor or pharmaceutical compositions thereof can be administered to a subject by any suitable route. For example, the compositions can be administered nasally, rectally, intracisternally, intraperitoneally, transdermally (as by powders, ointments, or drops), and/or parenterally. As used herein, "parenteral" administration refers to modes of administration other than through the gastrointestinal tract, which includes intravenous, intramuscular, intraperitoneal, intrasternal, intramammary, intraocular, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

In an embodiment, the present subject matter relates to a pharmaceutical composition, comprising a therapeutically effective amount of the MERS-COV inhibitor as described herein and a pharmaceutically acceptable carrier. In this regard, the pharmaceutically acceptable carrier can be one or more pharmaceutically acceptable carriers, excipients, or vehicles. In some embodiments, the present compositions can be used for combination therapy, where other therapeutic and/or prophylactic ingredients can be included therein.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 23rd Edition. Easton, Pa., Mack Publishing Company, 2020, the entire contents of which are incorporated by reference herein.

While human dosage levels have yet to be optimized for the MERS-COV inhibitor, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present multi-functional agents for treatment of a disease, disorder, or condition, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present multi-functional agents can also be administered in sustained or controlled release dosage forms, including depot injections, osmotic pumps, pills, transdermal (including electrotransport) patches, and the like, for the prolonged administration of the multi-functional agents at a predetermined rate, preferably in unit dosage forms suitable for single administration of precise dosages.

The present multi-functional agents may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the MERS-COV inhibitor, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active multi-functional agent as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active multi-functional agent in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active multi-functional agent contained in such parenteral compositions is highly dependent on the specific nature thereof, as well as the activity of the multi-functional agent and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the MERS CoV inhibitor alone or in combination with other pharmaceutically acceptable excipients can also be administered.

Formulations of the active MERS-COV inhibitor may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

As described herein, using fluorescence TSA, the thermal stability of MERS-CoV PLpro was assessed against gradient thermal denaturation. TSA is an efficient and dependable method for examining the protein-binding affinities and inhibitory effects of various chemicals. The Tm ranged from 7.66° C. to 20.09° C., and FIS demonstrated continuous inhibition at different dosages, according to the thermal shift experiment. The binding affinity made it abundantly clear that FIS is a viable candidate for further development and preclinical testing, and the apparent shift in the unfolding temperature of MERS-COV PLpro may be brought on by the precise and logical interaction of FIS with the protease. FIS significantly reduced the thermal stability of MERS-COV PLpro which may be due to its binding site at β-strands of N-terminal ubiquitin-like (Ubl) domain or other domain which reduced the structural stability of the protease and reduced the catalytic activity (unlike Dimethyl sulfoxide in SARS which increases the catalytic activity).

Polyphenols like Broussochalcone A, herbacetin, isobavachalcone, quercetin 3-β-d-glucoside, and helichrysetin have shown to be effective against MERS-COV cysteine proteases (3CLpro and PLpro) but there is no stability assay to determine the change in melting temperature. In a recent review, collective data showed 69 natural Flavonoids inhibit SARS proteases (3CLpro and PLpro), mainly by FRET assay. YM155, cryptotanshinone, tanshinone I, and GRL0617, were demonstrated to be potent SARS-COV PLpro inhibitors by FRET assay, with melting temperature varying from −8.72° C. to 4.88° C. The compounds which demonstrated protease inhibition did not necessarily change the ΔTm. In another study, protease inhibitors like lopinavir, ritonavir, atazanavir and nelfinavir lowered the ΔTm in HIV-protease thermal shift assay.

The stabilizing impact of a ligand is determined by the specific collection of conformational states that precisely interact with the ligand across the entire conformational image of the protein. The impact on protein stability will be negligible if the ligand has interatomic affinities with the majority of conformational states. A destabilizing effect might be anticipated if the preference for the nonnative states is stronger and the ligand is interatomic with a significant proportion of unfolded forms in addition to the native state. The FIS molecule is likely to bind to the PLpro thumb domain and prevent the protease from catalyzing. Moreover, binding to this region might increase the stability of the tertiary structure. The thermal stability assay described herein suggested that binding to this area might also stabilize the tertiary structure (i.e., raise the Tm) of MERS-COV PLpro.

In addition, FIS was virtually checked against MERS-COV PLpro for non-covalent interactions, which combined with numerous docking rounds, led to the identification of protein-ligand binding. Binding affinity, location, and poses against the MERS-COV PLpro were established, and experimental data were used to validate the docking score. Although compounds from virtual screens have already been published in the literature for potential testing against MERS-COV, most of them were docking studies, and the experimental evidence to support the in-silico study was scarce. Moreover, docking has often been done against the PLpro catalytic site rather than the other binding site, which is noticeably different from that described herein.

Figure 3A:
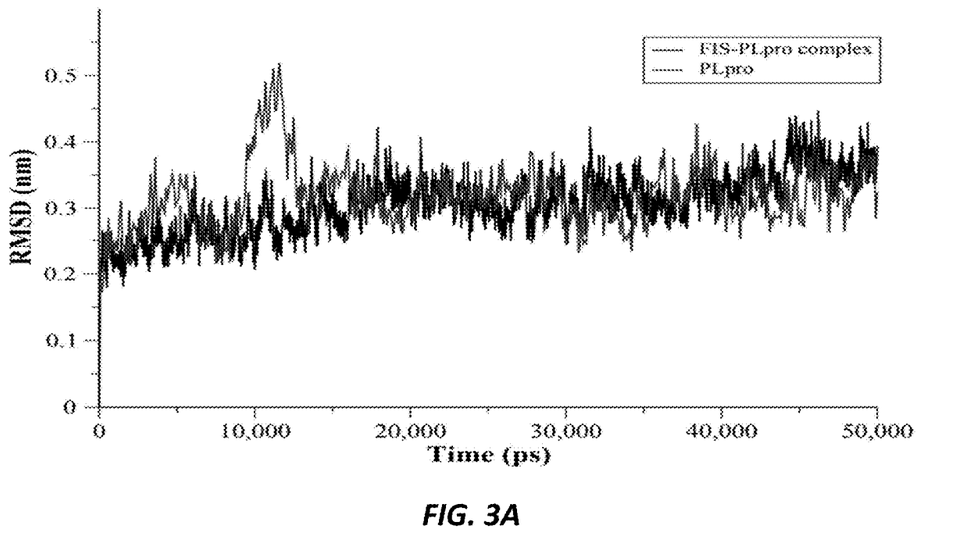
Figure 3B:
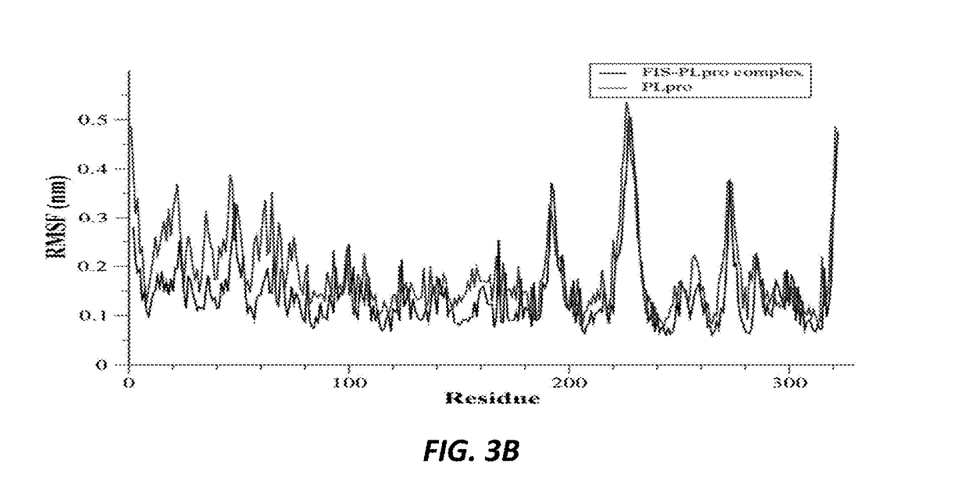
Figure 3C:
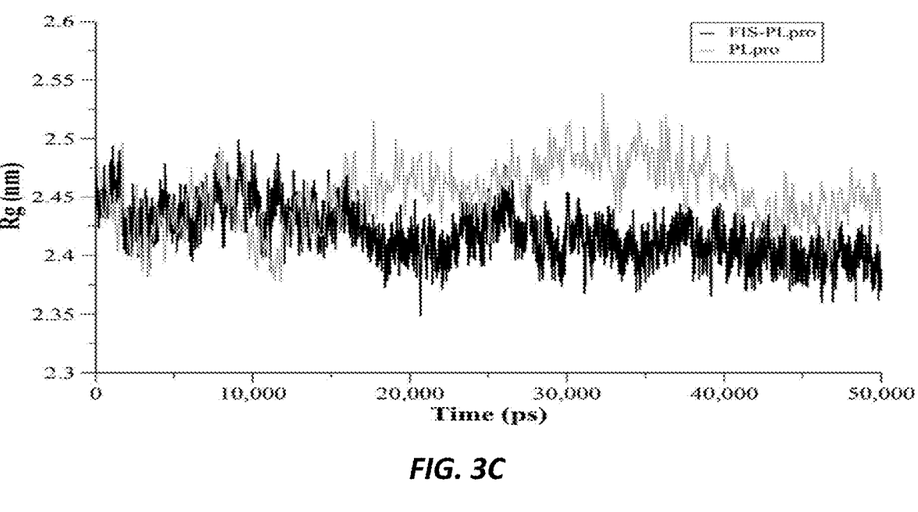
(FIG. 3C) radius of gyration (rg) for MERS CoV-PLpro and Fisetin-MERS-COV PLpro complex.

Thus, it is believed that the N-terminal ubiquitin-like (Ubl) domain of MERS-CoV PLpro contains the FIS binding site (FIGS. 3A-3C). There were two bi-cation interactions with the FIS rings as well as hydrogen bonds created by the MERS-COV PLpro S144, D143, G142, H139, and K138 residues with the FIS molecule (FIGS. 3A-3C). The -strands of the N-terminal ubiquitin-like (Ubl) domain of MERS-COV PLpro have been proposed as another potential binding site for FIS, but they may be the most likely candidate. This is because the domain is proximate to the MERS-COV PLpro catalytic triad and because FIS, as the heat assay results reveal, can cause MERS-COV PLpro to become unstable.

Because FIS is an antioxidant molecule with well-known pharmacokinetic and pharmacodynamic effects, it is possible to add it to a diet full of other foods to cure MERS-COV. As demonstrated in the experimental results described herein, FIS has the ability to precisely target MERS-COV PLpro and limit its catalytic activity The present teachings are illustrated by the following examples.

EXAMPLES

Example 1

Materials and Methods

Chemicals: Z-RLRGG-AMC acetate was bought from Bachem (CA, United States), provided the sinapic acid Carbosynth Ltd. (United Kingdom). MagicMedia and SYPRO™ dye were purchased from Thermo Fisher Scientific, Invitrogen (Rockford, Illinois, United States) sold Pierce™ BCA Protein Assay Kit. All other additional chemicals were of the analytical grade.

Protein expression and purification: The sequence of the MERS-COV PLpro, expression and purification were done according to our previously published report Alaofi et al., Briefly, cells were cultured in MagicMedia in presence of Kanamycin 50 μg/ml for 18 hours at 30° C. Cells were harvested by centrifugation and lysed by sonication in a buffer containing 50 mM Tris-HCl, 250 mM NaCl, 10 mM Imidazole, 2 mM Beta-mercaptoethanol (BME), 5% (v/v) glycerol, and phenylmethylsulfonyl fluoride, pH 8.0. Polyhistidine-tagged MERS-COV PLpro were eluted using 50 mM Tris-HCl, 250 mM NaCl, 200 mM Imidazole, 2 mM BME. The elutes were then dialyzed overnight and concentrated with Amicon, its concentration calculated using Pierce™ BCA Protein Experiment Kit.

MERS-COV PLpro inhibition assay MERS-COV PLpro inhibition assay was performed according to the protocol described previously. Briefly, increase in fluorescence was measured the hydrolysis of the fluorogeneic peptide Z-RLRGG-AMC-peptide by protease enzyme. A 384-well plate assay with a black, flat bottom was used to calculate the IC50 values for FIS. The 50 μL reactions mixture contained 20 mM Tris-buffer, 30 μM substrate Z-RLRGG-AMC, 60 nM MERS-COV PLpro enzyme and FIS at various concentration pH 8.0. Gain is 40, emission is 460 nm, and excitation is 360 nm. The fluorescence was measured at Excitation=360 nm; emission=460 nm; gain=40 for 60 minutes in Biotek HT Microplate Reader (USA).

Thermal shift assay (TSA) Using Applied Biosystems™ 7500 Real-Time PCR Systems, differential scanning fluorimetry (DSF) was used to determine the amount of FIS binding to the MERS CoV PLpro protein. Shortly after being diluted into a reaction buffer to a final concentration of 2 mol/L, testing chemicals ranging from 1.36 to 1746.85 μM were added, and the mixture was incubated at 25° C. for 30 min. buffer served as a point of reference. Using SYPRO orange dye, a temperature gradient between 25 and 95° C. with an incremental step of 1° C./minute was applied, and the fluorescence signal was recorded. The difference between the melting temperature (Tm) in the presence of testing compounds and the melting temperature (Tm) in the presence of buffer and protein was used to calculate the melting temperature (Tm), which was calculated as the mid log of the transition phase from the native to the denatured protein using a Boltzmann model in Protein Thermal Shift Software v1.3.

MD simulations To evaluate the binding of Fisetin with PLpro, we ran MD simulations for Fisetin-PLpro complex and PLpro using GROMACS 5.1.4 program with CHARMM36 force field [61]. PLpro starting coordinate was obtained from Protein Data Bank (PDB ID 4RNA). Ligand (Fisetin) topology was prepared using the CHARMM General Force Field (CGenFF) online server. Afterward, the Fisetin-PLpro complex coordinate system was prepared as well as the PLpro system. Fisetin-PLpro or PLpro systems were solvated in a dodecahedron box with TIP3P water molecules following our previous work. Titratable residues' ionization states were allocated in accordance with a pH 7.0 condition. By substituting sodium and chloride ions for water molecules, the ionic strength was simulated to be 0.15 M. Energy minimization using the steepest descent approach was carried out and each system was at energy minimum. Afterward, equilibration of both systems was done similarly in NVT followed by NPT to achieve well-equilibrated systems at the desired temperature and pressure. However, restraints to the ligand (Fisetin) were applied before equilibrating the Fisetin-PLpro complex system as well as proper treatment of temperature coupling groups. Finally, after release of the position restraints, a 50 ns-long production MD simulations was to be performed.

Example 2

Protein Expression and Purification

We initially expressed MERS-COV PLpro in *E. coli* to assess the inhibitory effect of FIS against the MERS-COV. We utilized SDS-PAGE analysis to confirm the purity and molecular weight of MERS-COV PLpro. A 37 kDa recombinant protein was observed by culturing in Magic Media at 30° C. for 18 hours, this was used to confirm expression. In comparison to washing buffer the purification column procedure produced higher purified rMERS-PLpro protein. We successfully expressed the MERS-PLpro gene at high levels in BL21 DE3 *E. coli* self-induced culture. Using His-tag primary monoclonal antibody (SC-8036), Western blot analysis of the MERS-PLpro with N-terminal His-Tag was carried out, and the existence of MERS-PLpro recombinant protein was confirmed.

Example 3

MERS-COV PLpro Inhibition by FIS

Figure 1A:
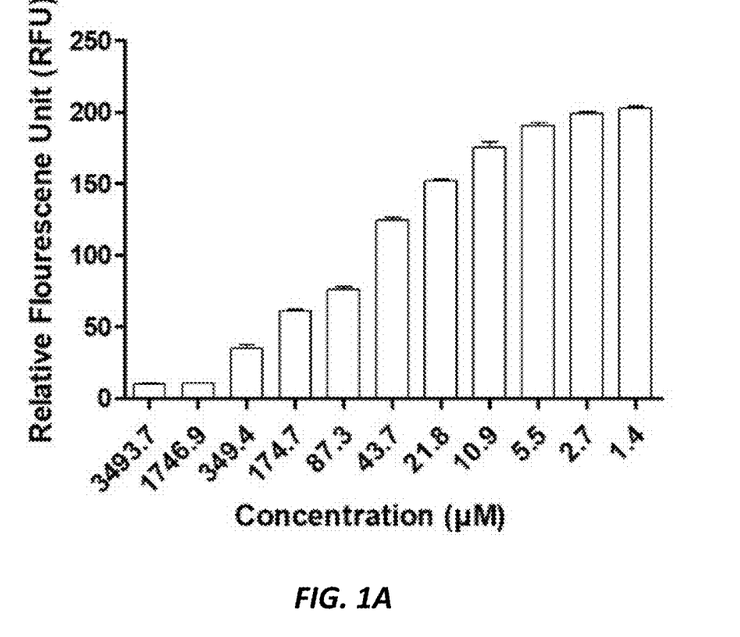
Figure 1B:
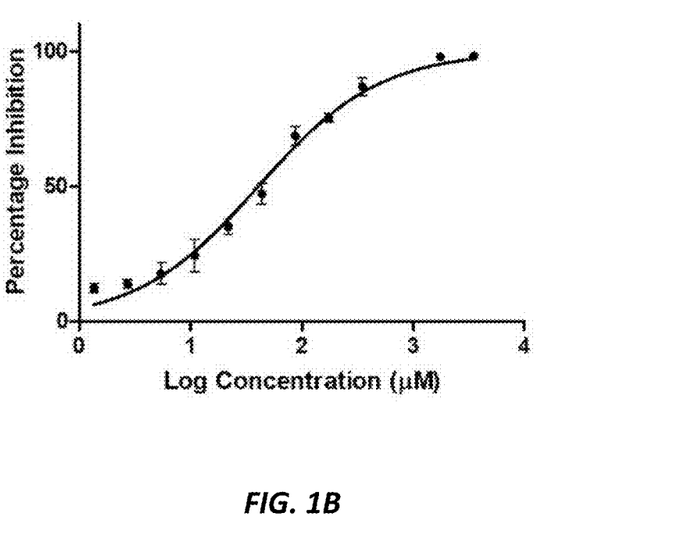
(FIG. 1B) dose response curve of MERS-COV PLpro inhibition identified from the IC50 protease inhibition assay with dissociation of Z-RLRGG-AMC substrate, (values represent the average±standard deviation of three replicates).

Protease inhibition is a dependable and effective way to assess a drug's ability to inhibit different viral proteases. In order to determine how well the FIS inhibits MERS-COV PLpro, fluorescence from the AMC moiety was measured as part of a dose-dependent protease inhibition assay. Enzymatic activity was assessed using the accepted method for the continuous enzymatic inhibition test, and inhibition curves were constructed by holding enzyme and substrate concentrations constant while varying the amount of the drug (FIGS. 1A-1B). When FIS was used at various concentrations, its enzymatic inhibitory activity was assessed by looking at the first slope of each curve (FIG. 1B). It's important to note that FIS all affected enzyme activity in a dose-dependent manner (FIG. 1A-B). The non-linear regression analysis employing a simple inhibition model allowed for the determination of an apparent inhibition at different dose and time points. FIS's IC50 values of 40.58 UM after 30 minutes of incubation are shown in Table 1.

TABLE 1

| $IC_{50}$ of MERS-$C_OV$ PLpro inhibition identified by dissociation of Z-RLRGG-AMC substrate against FIS | |
|---|---|
| Title 1 | FIS |
| $IC_{50}$ (µM) | 40.58 |

Previously, doxorubicin and acyclovir were tested and only the former showed inhibitory effect against MERS-PLpro. Here, fisetin showed a similar inhibitory effect of doxorubicin while metformin was not effective. Interestingly, fisetin and doxorubicin share similar structural components while metformin and acyclovir have nitrogen-based entities.

Example 4

Stability Evaluation of MERS-COV PLpro-FIS Complex by Thermal Shift Assay

TSA is a reliable, adaptable method that is favoured over alternative stability study procedures in high throughput screening due to its high rate of reproducibility, ligand binding, and evaluation of protein stabilization at a faster rate. Despite the fact that FIS inhibited the MERS-PLpro in a dose-dependent and particular manner, we confirmed our discovery by doing a thermal shift investigation of the protein's stability and ligand interactions, where we found that the results were uniform. The basic procedure of a thermal shift experiment involves the incubation of natively folded proteins in SYPRO Orange. By carefully increasing the temperature and measuring the SYPRO Orange fluorescence emission at the same time, it is able to monitor the thermal denaturation of the protein in the presence of ligands.

The variation in melting temperature ($\Delta Tm$) (mean=13.94° C.) for various concentrations for FIS ranged from 7.66° C. to 20.09° C. Their enzymatic protease inhibition is compatible with the thermal shift assay. In contrast, FIS decreased protein stability by approximately 7.66° C. to 20.09° C. in the TSA experiment and showed an IC50 value for protease inhibition of 40.58 µM (Table 2 and FIGS. 2A-2D).

TABLE 2

| $IC_{50}$ of MERS-$C_OV$ PLpro inhibition identified by dissociation of Z-RLRGG-AMC substrate against FIS. | |
|---|---|
| Title 1 | FIS |
| $IC_{50}$ (µM) | 40.58 |

Figure 2A:
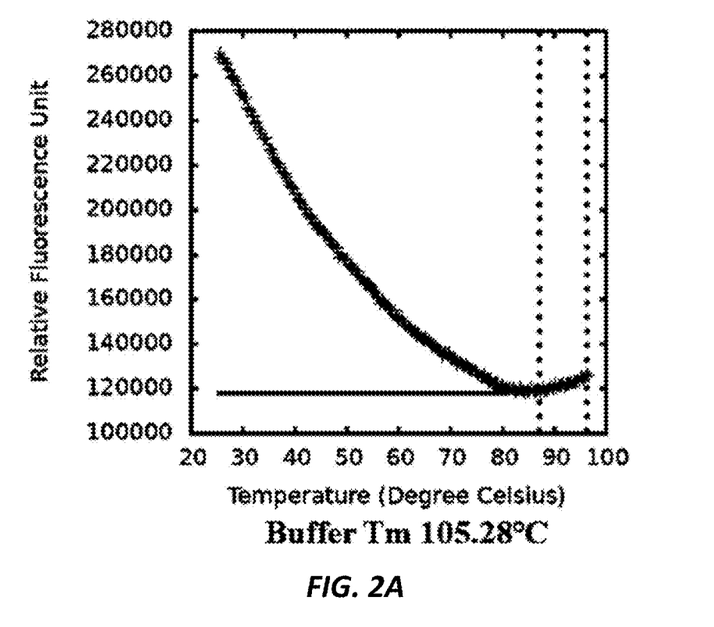
FIGS. 2A-2D are graphs showing thermal denaturation curves and melting temperature (Tm) by Thermal Shift Assay (TSA) of (FIG. 2A) buffer, (FIG. 2B) MERS PLPro, (FIG. 2C) MERS PLpro+Metformin, and (FIG. 2D) MERS PLpro+fisetin.
Figure 2B:
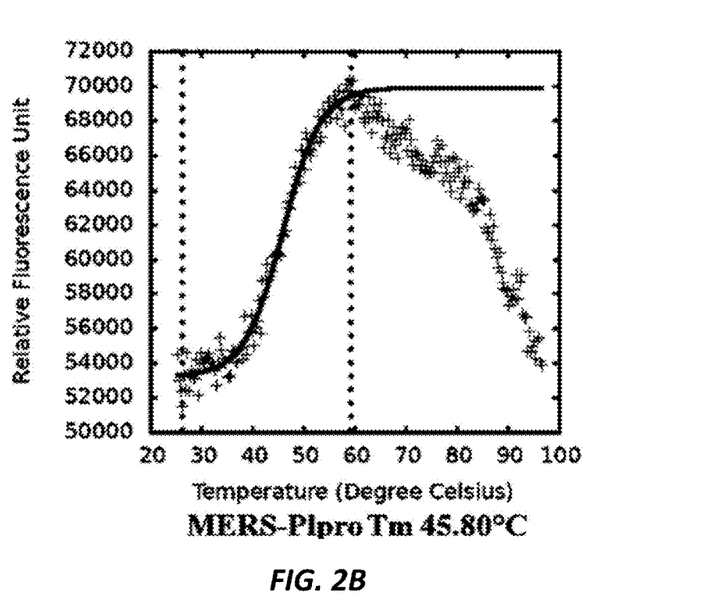
Figure 2C:
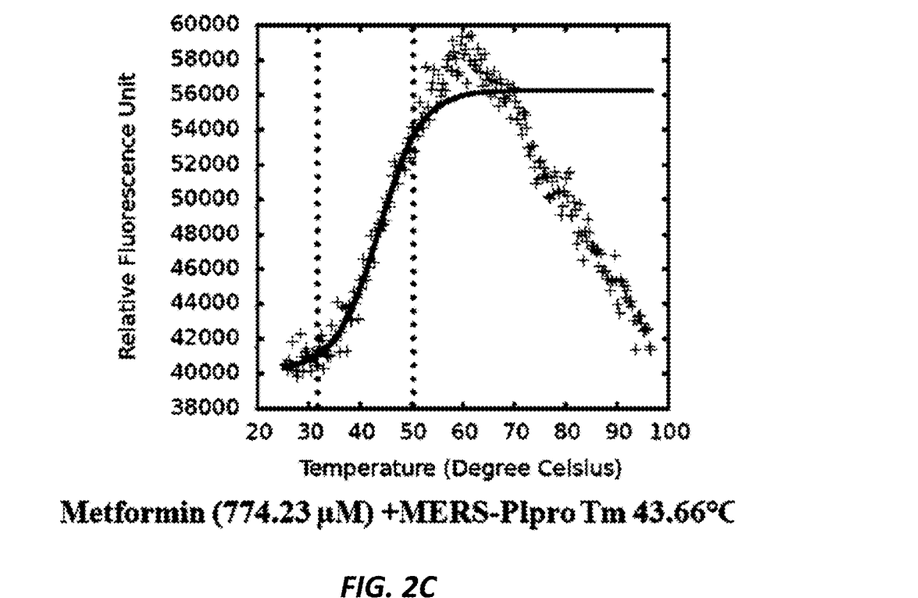
Figure 2D:
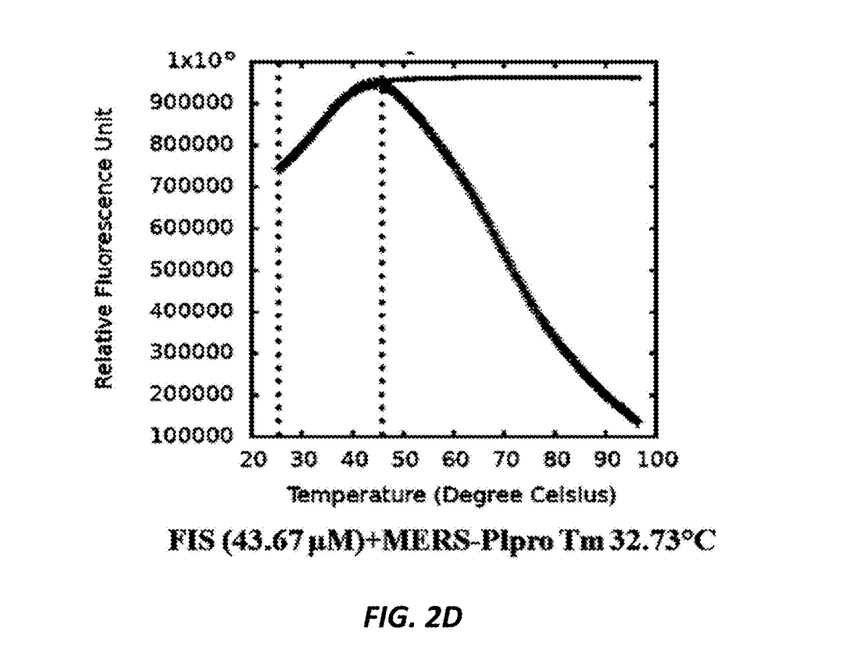

Both of the studies studies showing FIS's ability to suppress MERS-PLpro are consistent with the fact that it is dose-dependent. It is worth mentioning Metformin did not alter the Tm of MERS-PLpro at any concentration, suggesting that there may not have been any interaction between Metformin and PLpro (FIG. 2D). In contrast, FIS decreased protein stability by roughly 12-18° C. in the TSA experiment and showed an IC50 value for protease inhibition of 40.58 µM (FIGS. 2A-2D). Interestingly, FIS lowered the $\Delta Tm$ by ~13° C. at IC50 concentration unlike doxorubicin, in our previous finding, which increased the melting temperature by ~20° C. This can be due to the two molecules initiating different effects on MERS-PLpro conformation.

Example 5

Md Simulations of Fisetin-PLpro Complex Assessment

Root mean square fluctuation (RMSF) was calculated for PLpro with and without fisetin. Overall, PLpro showed more rigid structure in presence of fisetin in comparison to PLpro (FIG. 3A). In XX18-XX22, XX20-XX80, XX48-XX68, XX260 showed rigid regions in Fisetin-PLpro compared to PLpro. RMSF values were decreased by 0.9 to 1.5 Å indicated to significant effect of fisetin on PLpro structure (FIG. 3B). Radius of gyration (Rg) was used to assess PLpro flexibility conformation in presence of fisetin molecule. Rg of PLpro was significantly decreased with fisetin compared to free PLpro (FIG. 3C).

It is to be understood that the multi-functional agents are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating Middle East Respiratory Syndrome (MERS), comprising:
    administering a therapeutically effective amount of a pharmaceutical composition consisting of fisetin and a pharmaceutically acceptable carrier to a subject in need thereof;
wherein the fisetin binds to MERs-papain-like protease ($PL_{pro}$) and inhibits $PL_{pro}$ activity, thereby providing a treatment for MERS.

2. The method of claim 1, wherein the pharmaceutical composition is administered by a route selected from the group consisting of oral, nasal, rectal, intracisternal, intraperitoneal, transdermal, and parenteral.

3. The method of claim 1, wherein the subject is a mammal.

4. The method of claim 3, wherein the mammal is a human being.

* * * * *

SEQUENCE LISTING

```
Sequence total quantity: 1
SEQ ID NO: 1          moltype = AA   length = 327
FEATURE               Location/Qualifiers
source                1..327
                      mol_type = protein
                      organism = Homo sapiens
SEQUENCE: 1
LTIEVLVTVD GVNFRTVVLN NKNTYRSQLG CVFFNGADIS DTIPDEKQNG HSLYLADNLT    60
ADETKALKEL YGPVDPTFLH RFYSLKAAVH GWKMVVCDKV RSLKLSDNNC YLNAVIMTLD   120
LLKDIKFVIP ALQHAFMKHK GGDSTDFIAL IMAYGNCTFG APDDASRLLH TVLAKAELCC   180
SARMVWREWC NVCGIKDVVL QGLKACCYVG VQTVEDLRAR MTYVCQCGGE RHRQLVEHTT   240
PWLLLSGTPN EKLVTTSTAP DFVAFNVFQG IETAVGHYVH ARLKGGLILK FDSGTVSKTS   300
DWKCKVTDVL FPGQKYSSDC NHHHHHH                                      327
```